United States Patent
Casarotto

(10) Patent No.: US 10,758,115 B2
(45) Date of Patent: Sep. 1, 2020

(54) MINI-INVASIVE DEVICE FOR THE ENDOUROLOGIC TREATMENT

(71) Applicant: FMP Biotechnologies S.r.l., Vicenza (IT)

(72) Inventor: Guido Casarotto, Vicenza (IT)

(*) Notice: Subject to any disclaimer, the term of this patent is extended or adjusted under 35 U.S.C. 154(b) by 0 days.

(21) Appl. No.: 16/302,634

(22) PCT Filed: May 25, 2017

(86) PCT No.: PCT/IB2017/053085
§ 371 (c)(1),
(2) Date: Nov. 17, 2018

(87) PCT Pub. No.: WO2017/203462
PCT Pub. Date: Nov. 30, 2017

(65) Prior Publication Data
US 2019/0142266 A1    May 16, 2019

(30) Foreign Application Priority Data

May 26, 2016  (IT) ................. UA2016A3838

(51) Int. Cl.
| | |
|---|---|
| A61B 1/307 | (2006.01) |
| A61B 17/22 | (2006.01) |
| A61B 1/018 | (2006.01) |
| A61B 1/07 | (2006.01) |
| A61B 18/26 | (2006.01) |

(Continued)

(52) U.S. Cl.
CPC .............. *A61B 1/307* (2013.01); *A61B 1/018* (2013.01); *A61B 1/07* (2013.01); *A61B 17/22* (2013.01); *A61B 17/22031* (2013.01); *A61B 18/26* (2013.01); *A61B 2017/0034* (2013.01); *A61B 2017/00424* (2013.01); *A61B 2017/2215* (2013.01); *A61B 2017/22079* (2013.01); *A61B 2017/22082* (2013.01); *A61B 2018/00511* (2013.01); *A61B 2018/00517* (2013.01); *A61B 2218/007* (2013.01)

(58) Field of Classification Search
CPC ........... A61B 1/307; A61B 1/018; A61B 1/07; A61B 1/22031; A61B 18/26
See application file for complete search history.

(56) References Cited

U.S. PATENT DOCUMENTS

| | | | |
|---|---|---|---|
| 4,692,139 A | 9/1987 | Stiles | |
| 4,798,193 A * | 1/1989 | Giesy | ............... A61M 25/0105 600/114 |

(Continued)

FOREIGN PATENT DOCUMENTS

| | | | |
|---|---|---|---|
| DE | 3633527 A1 | 4/1988 | |
| DE | 19842113 A1 | 3/2000 | |

*Primary Examiner* — Timothy J Neal
*Assistant Examiner* — Jae Woo
(74) *Attorney, Agent, or Firm* — Themis Law

(57) ABSTRACT

A mini-invasive device for endourologic treatment includes a tubular conduit, longitudinally flexible, configured to be inserted through and along the operating channel of an endoscope. The tubular conduit internally defines an essentially non-deformable lumen, has a proximal portion having a connector to a suction device, has a distal portion intended to project from the distal tip of the endoscope, and internally delimits a suction conduit, within which at least one tool can be removably inserted to be used in endourologic treatment.

19 Claims, 5 Drawing Sheets

(51) Int. Cl.
*A61B 17/221* (2006.01)
*A61B 17/00* (2006.01)
*A61B 18/00* (2006.01)

(56) References Cited

U.S. PATENT DOCUMENTS

| | | | | |
|---|---|---|---|---|
| 4,971,033 | A * | 11/1990 | Ehlers | A61B 1/0056 600/139 |
| 5,025,778 | A * | 6/1991 | Silverstein | A61B 1/0008 600/104 |
| 5,231,989 | A * | 8/1993 | Middleman | A61B 1/00165 600/434 |
| 5,247,938 | A * | 9/1993 | Silverstein | A61B 1/018 600/459 |
| 5,396,880 | A * | 3/1995 | Kagan | A61B 1/0051 600/109 |
| 5,417,697 | A | 5/1995 | Wilk et al. | |
| 5,938,587 | A * | 8/1999 | Taylor | A61B 1/018 138/118 |
| 6,464,632 | B1 * | 10/2002 | Taylor | A61B 1/005 138/174 |
| 7,540,868 | B2 | 6/2009 | Elliott et al. | |
| 8,182,422 | B2 * | 5/2012 | Bayer | A61B 1/00016 600/109 |
| 2004/0019358 | A1 * | 1/2004 | Kear | A61B 17/22031 606/127 |
| 2006/0173407 | A1 * | 8/2006 | Shaughnessy | A61B 1/00158 604/95.01 |
| 2007/0142711 | A1 * | 6/2007 | Bayer | A61B 1/00016 600/175 |
| 2007/0270649 | A1 * | 11/2007 | Long | A61B 1/00078 600/144 |
| 2008/0183038 | A1 * | 7/2008 | Tilson | A61B 1/018 600/104 |
| 2008/0188868 | A1 * | 8/2008 | Weitzner | A61B 1/0014 606/130 |
| 2011/0022172 | A1 * | 1/2011 | Gonzales | A61B 17/24 623/10 |
| 2011/0087234 | A1 * | 4/2011 | Ayala | A61B 1/018 606/108 |
| 2011/0213297 | A1 | 9/2011 | Aklog et al. | |
| 2012/0143006 | A1 * | 6/2012 | Avitsian | A61B 1/00066 600/121 |
| 2016/0045208 | A1 | 2/2016 | Ciulla | |

\* cited by examiner

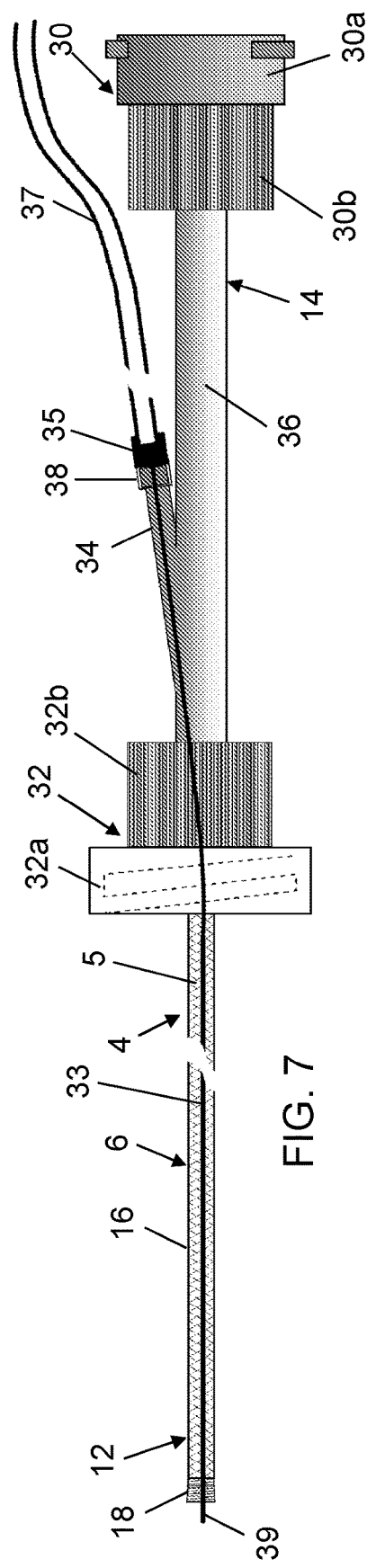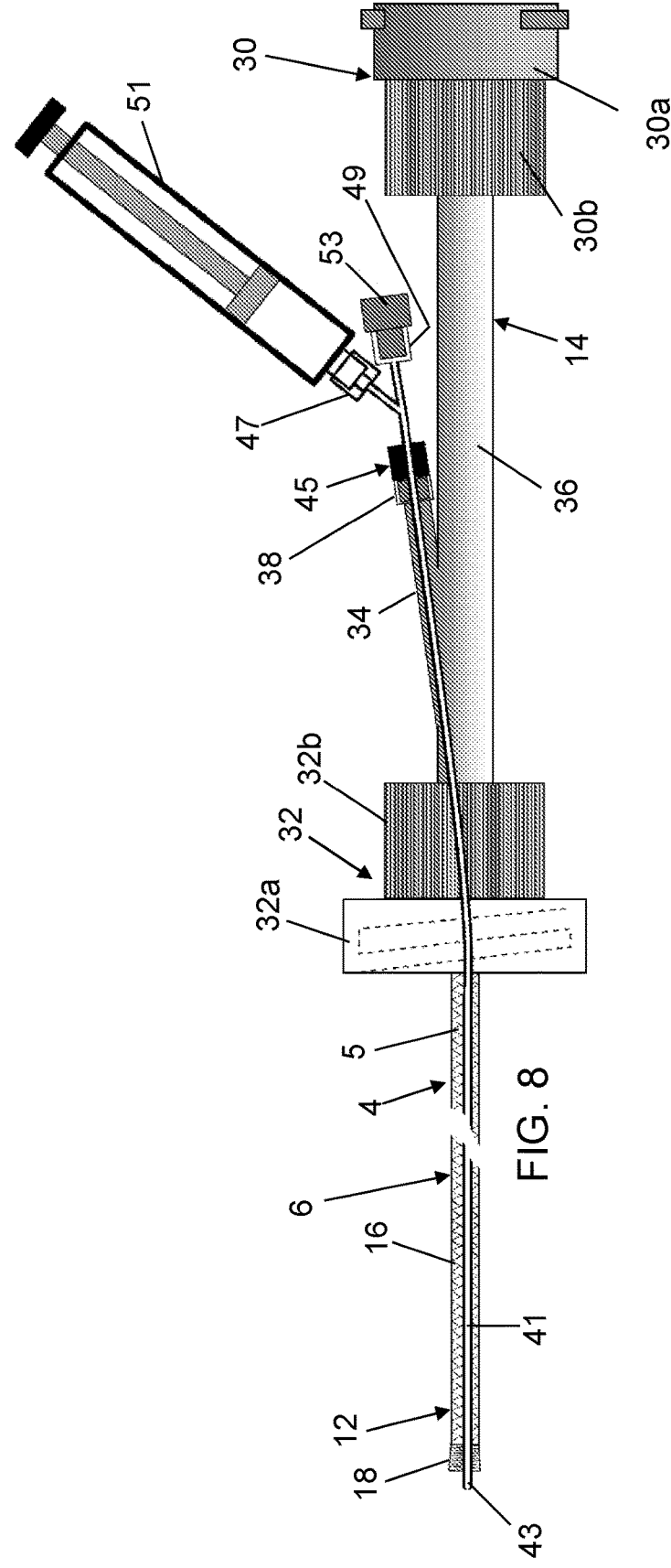

MINI-INVASIVE DEVICE FOR THE ENDOUROLOGIC TREATMENT

FIELD OF THE INVENTION

The present invention relates to a mini-invasive device for endourologic treatments.

BACKGROUND OF THE INVENTION

At present, the endourologic treatment of urinary calculosis provides for the introduction, within the operating channel of specific endoscopes, of tools useful for the treatment of calculosis itself. These tools are essentially divided into two types: those adapted to reduce the stone in a series of fragments of suitable dimensions suitable for natural extraction by the human body, and those aimed at mobilizing the stone itself or at the direct extraction of the fragments.

Among the devices of this second type are grippers specifically designed to grab the stone fragments. In particular, the largest endoscopes, with a rigid structure, allow the use of very large grippers, which are particularly effective in terms of grip and extraction. Moreover, also small endoscopes, with a flexible structure, allow the passage of small grippers within their operating channel.

While grippers are economically advantageous in that, after sterilization, can be reused, they are nevertheless ineffective in most cases. In particular, the grippers, due to their specific conformation as well as to the material of which they are made, once introduced inside the endoscope cause the stiffening of the latter and a reduction in its flexibility. This greatly affects the effectiveness of the endoscope itself, limiting its ability to reach peripheral areas of the urinary tract, especially in cases where the target stone is "out of axis", that is, misaligned with respect to the entrance of the endoscope.

Moreover, the operation of the grippers is compromised beyond a certain curvature thereof. In particular, beyond a certain limit value, the angularity of the bearing structure compromises the transmission of the mechanical control from the handpiece to the clamps of the grippers, thereby preventing the opening of the mouth thereof.

As an alternative to grippers, among the devices aimed at mobilizing the stone and/or at the direct extraction of the fragments thereof, the so-called baskets are also known. These are extremely thin and flexible devices that can be introduced into the body through the endoscope's operating channel. They are manouvrable through an outer handpiece that controls the opening of metal coils on the lithiasic fragment. In particular, such coils, by reclosing themselves as a network on the target stone fragment, envelop it so as to allow the mobilization or extraction thereof.

The basket devices overcome all the drawbacks of grippers since, having a thinner structure, they compromise the flexibility of the endoscope in which they are introduced to a lesser extent. In addition, unlike the grippers, they can open on the target even under highly angled conditions.

However, also the basket devices are not completely satisfactory. Firstly, being disposable devices, they add a specific cost to each surgical procedure. In addition, it is often difficult to block the stone fragment within the coils, either because it is too large to be completely enveloped in the coils or, conversely, because the fragments are so small that they emerge from the coil loops, while the same close. In essence, basket devices cannot be used for the removal of particularly large or particularly small stone fragments.

A further drawback relates to the operational difficulty associated with the impossibility of enveloping the stone when the same is off the axis with respect to the opening of the basket coils.

In addition, after some steps and attempts to remove the lithiasis fragments, the basket operation is compromised, and this can lead to an extremely difficult release of the stone fragment, once it has been gripped, if it is considered too large to be extracted whole. Therefore, if the basket device operation is compromised, it must inevitably be replaced, with further economic expenditure. Moreover, the endoscopic maneuvers necessary to resolve this complication can be complex and cause in turn additional clinical complications.

Ultimately, all these technical and operational difficulties of the basket device involve a lengthening of the operating time.

US 2004/0019358 describes a device that includes an elongated element defining a hollow suction conduit. In particular, this elongated element is flexible lengthwise, is configured to be inserted within the operating channel of a ureteroscope and is also able to withstand the deformation caused by suction. More in detail, the proximal portion of the elongated element is in communication with a vacuum source able to provide the suction within the conduit, while the distal portion of the elongated element itself projects from the ureteroscope and is intended to come into contact with the object to be treated in the patient's body. US 2004/0019358 describes in detail the use of the elongated element for capturing, retaining, moving/removing a kidney stone when the latter is embedded in a tissue or is located in a part of the patient's body that is difficult to access using traditional instruments (baskets or grippers). However, in all these applications, it is provided that the conduit, defined within the elongated element, always and only acts as a suction conduit. In fact, US 2004/0019358 teaches at most to retract the elongated element from the ureteroscope and insert within the ureteroscope itself, as an alternative to the elongated element defining the suction conduit, another surgical instrument for removing the stone.

U.S. Pat. No. 5,102,415, WO 99/45835, US 2002/188313 and WO 2012/156924 relate to devices used in cardiology, not in the endourologic context. In particular, in the context of cardiology, the use of the endoscope is not involved and, therefore, the technical issues are different from those in the endourologic context, where the use of the endoscope is involved.

U.S. Pat. No. 6,375,651 describes a device that comprises a suction conduit and a conduit for energy transmission, which can be coextruded, attached to or separate from each other, or one inside the other. In addition, the casing of the device may accommodate a plurality of components, such as laser fibers, optical fibers and catheters and guide wires. However, in all the embodiments described in U.S. Pat. No. 6,375,651, there are always two conduits, one of suction and one for the laser fiber, which are separate from each other. In particular, the laser fiber conduit can also be placed within the suction conduit, but in any case they must be separate. Last but not least, the fact that the outer tubular casing, inside of which the suction conduit and the laser conduit are separately formed, internally has a particularly thick circular crown which has a particularly reduced flexibility lengthwise.

U.S. Pat. No. 7,540,868 describes a device provided with an elongated element connected to a suction tube and inside of which a laser fiber is inserted which is secured with a clip at the distal portion of the elongated element. The presence of the clip does not allow the removable insertion of the laser fiber and, in any case, does not allow the removable insertion of other gripping tools, such as grippers or the basket, used in endourologic treatments. In addition, U.S. Pat. No. 7,540,868 requires that the elongated element is connected to the suction connector via a suction tube, which is housed inside the casing of the device. Last but not least, the fact that the elongated element of U.S. Pat. No. 7,540,868 does not have a non-deformable inner lumen.

U.S. Pat. No. 4,692,139 describes a catheter for removing obstructions that are present in a biological channel that comprises an insertion sleeve (and not an endoscope) inside which a flexible vacuum tube is inserted which is connected with the proximal end thereof to a suction source. Moreover, a small tube is inserted within the suction tube for the injection of medical substances and an ultrasound probe. In this solution, the suction tube has on the outer surface a male thread that cooperates and engages with a corresponding female thread which is provided on the inner surface of the insertion sleeve in order to allow a controlled sliding of the suction tube inside the sleeve. Moreover, a locking ring of the distal end of the vacuum tube is provided at the distal tip of the sleeve in order to prevent the latter from protruding beyond the distal tip of the sleeve itself.

U.S. Pat. No. 5,417,697 describes a solution for removing a polyp from a patient's colon. This solution comprises a device for endoscopic surgery with an elongated tubular conduit insertable within a channel of an endoscope. In particular, at the distal end thereof, the tubular conduit has a cup-shaped portion from which a cauterization ring protrudes which is powered with electric current to cut the polyp from the patient. In addition, the tubular conduit is provided with suction to allow the polyp removed to enter within the conduit itself. As shown in the figures, the tubular conduit of U.S. Pat. No. 5,417,697 does not have a substantially non-deformable lumen, but indeed it must just be deformable in order to allow the entry of the polyp removed.

DE 19842113 describes a solution for extracting stents or blood clots from blood vessels. This solution comprises a first extraction catheter, which consists of a tubular conduit with three expandable portions at its distal tip which open to define a funnel. In particular, this extraction catheter is inserted through and entirely crosses a second introducer catheter, so that by protruding from the latter, the tip of the first one opens as a funnel. More in detail, the second introducer catheter consists of a cover sleeve, having smaller length than the extraction catheter and which is slidable along the latter. It is also possible to suction the clot within the extraction catheter and this means necessarily that the lumen of such a catheter should be deformable.

U.S. Pat. No. 5,417,697 and DE19842113 do not describe devices for the endourologic treatment and, in particular, it is clear that the deformability of the lumen of the tubular conduit of U.S. Pat. No. 5,417,697 of the extractor catheter of DE 19842113 makes these solutions unsuitable and incompatible with the needs and the suction values required in the endourologic context, for example for capturing and mobilizing the stones.

SUMMARY OF THE INVENTION

The object of the invention is to overcome all these drawbacks by providing a mini-invasive device for the endourologic treatment that overcomes the drawbacks of traditional devices and that is both alternative and ameliorative with respect to these.

Another object of the invention is to provide a device adapted to be used in combination with one or more tools used for the endourologic treatment, such as a lithotripsy laser source and/or a gripping tool and/or a catheter for injecting substances.

Another object of the invention is to provide a device which, while having a small size, is particularly effective and more specifically capable of reaching even the most peripheral districts of the urinary tract.

Another object of the invention is to provide a device that does not obstruct the flexibility of the endoscope within which it is inserted.

Another object of the invention is to implement a device that has high accuracy, reliability and safety.

Another object of the invention is to implement a device that is multifunctional and that reduces the surgery time.

Another object of the invention is to implement a device with an alternative characterization, in constructional, functional and performance terms, compared to the traditional ones.

Another object of the invention is to implement a device that can be obtained in a simple, quick and cost-effective manner.

These objects, both alone or in any combination thereof, and others that will appear from the following description are achieved, according to the invention, with a device having the features described hereinafter.

BRIEF DESCRIPTION OF THE DRAWINGS

The present invention is further clarified hereinafter in a preferred embodiment thereof described by way of non-limiting example only with reference to the accompanying drawings, in which:

FIG. 7 shows a schematic enlarged view of the device according to the invention in which a laser fiber used in the endourologic treatment has been inserted, FIG. 8 shows a schematic enlarged view of the device according to the invention in which an injection catheter used in the endourologic treatment has been inserted.

DETAILED DESCRIPTION OF EMBODIMENTS OF THE INVENTION

Figure 1:
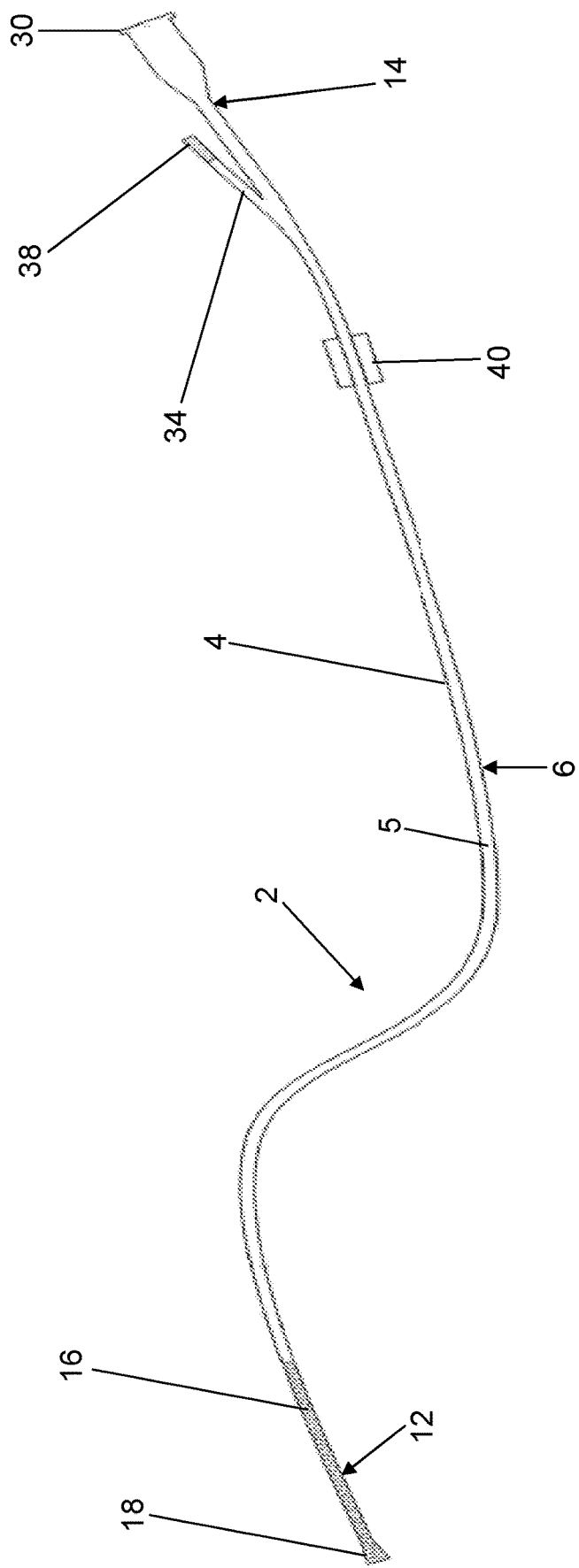
FIG. 1 shows a schematic view of the device according to the invention.
Figure 2:
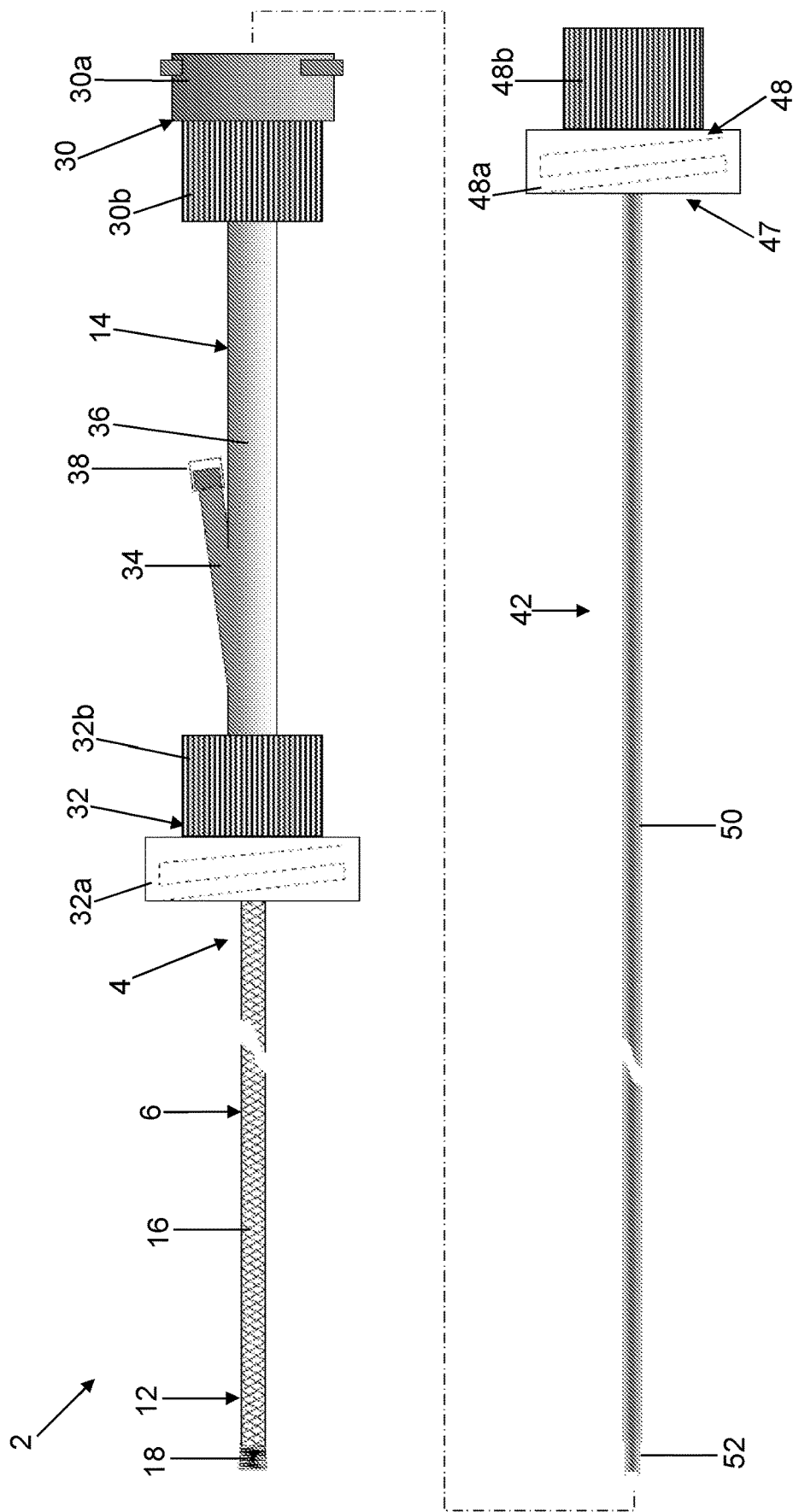
FIG. 2 shows a schematic and detailed view of the components of the device in FIG. 1.
Figure 3:
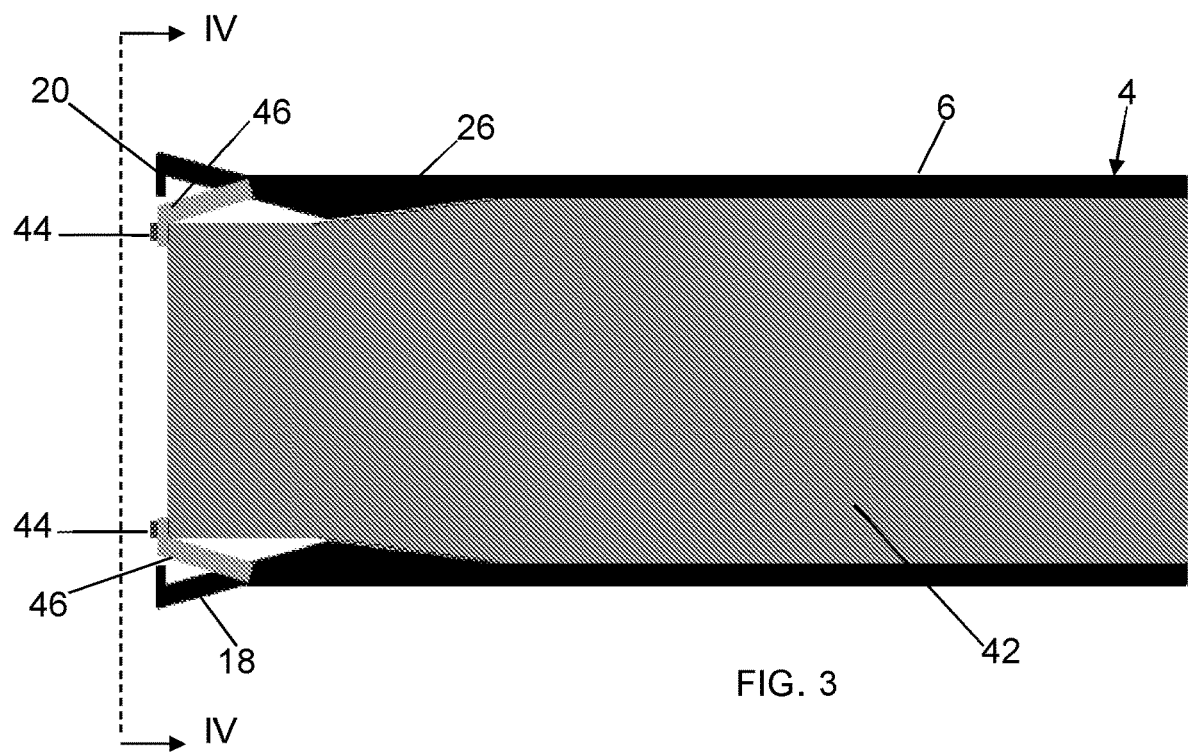
FIG. 3 shows a longitudinal section of an enlarged detail of the distal end of the device in FIG. 1 with a guide inserted therein.
Figure 4:
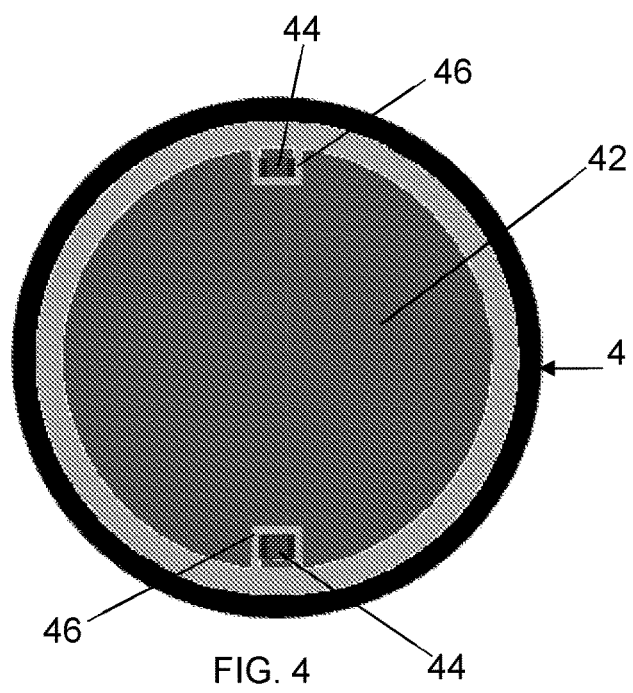
FIG. 4 shows it according to view IV-IV in FIG. 3.

As can be seen in the figures, the mini-invasive device 2 according to the invention comprises a tubular conduit 4 having:

a central portion 6 intended to cross the entire operating channel 8 of an endoscope 10, a portion 12 which in operation is distal and is intended to project from the inner end of endoscope 10, inserted in the patient's body, in order to reach the target to be treated, a portion 14 which in operation is the proximal one and is intended to project from the outer end of endoscope 10 and to be connected to suction means, not shown.

The tubular conduit 4 internally delimits a suction conduit 5 and, within the latter, one or more tools used in the endourologic treatment and can be removably inserted, preferably a laser source 33 for lithotripsy, a gripping tool and/or a catheter 41 for injecting substances. Suitably, the suction conduit 5, defined by the tubular conduit 4, is configured so that multiple tools used in the endourologic treatment can be inserted simultaneously within the conduit itself or one at a time.

Advantageously, the suction conduit 5, within which at least one tool used in the endourologic treatment can be removably inserted, is entirely and solely delimited by the inner walls of the tubular conduit 4.

The tubular conduit 4 of device 2 has a high longitudinal flexibility, substantially along its entire longitudinal development, and at the same time has a high transverse deformability, i.e. it is able to maintain the lumen defined therein unaltered even when it is subjected to contraction forces due to internal suction, and/or to compression forces caused by the irrigation flow, which acts on the outer surface of the conduit itself.

Preferably, the distal portion 12 of the tubular conduit 4 has greater longitudinal flexibility than the remaining part of the tubular conduit itself. More in detail, the central 6 and/or proximal 14 portions of the tubular conduit 4 have such longitudinal flexibility features as to allow a radius of curvature of at least 20 cm substantially by the whole length thereof, while the distal portion 12 of said conduit 4, which is preferably about 10 cm long, has a greater flexibility such as to allow reaching a radius of curvature of about 1.5 cm.

The tubular conduit 4 is made of thin and biocompatible plastic material, for example polytetrafluoroethylene (PTFE), polyether block amide (PEBA), thermoplastic polymers with highly flexible medical grade, polyurethane (PU), polyethylene (PE) and/or other materials commonly used for the manufacture of medical tubes and catheters.

Inside the tubular conduit 4, which comprises the central 6, distal 12 and proximal 14 portions, a reinforcement armor 16 may advantageously be associated. It may preferably be made of metal, for example titanium alloys, Nitinol or other high-flexibility metals with thermal memory and is designed to ensure the non-deformability of the inner lumen; to this end, it may have a spiral or "X" mesh crossed pattern, developing by the entire tubular conduit 4 or, alternatively, only in certain areas, specifically in the distal portion 12.

In particular, said longitudinal flexibility and transverse non-deformability features of the tubular conduit 4 mainly derive from the elastic modulus of the material of which the conduit itself is made and/or from the density and type ("X" meshes or spiral) of the reinforcement armor 16.

The central portion 6 of the tubular conduit 4 has a substantially constant diameter 24 throughout the entire development thereof. Preferably, the central portion 6 of the tubular conduit 4 is made with a mesh of Nitinol coated with hydrophilic PTFE; this allows a high flowability of the flows internal and external to the conduit as well as a high longitudinal flexibility and a high transverse non-deformability.

The distal portion 12 of the tubular conduit 4, that is, the portion intended to project from endoscope 10 to reach the target, consisting, for example, of a stone fragment to be mobilized or to be removed, comprises a truncated-cone termination 18 extending outwards so as to define a greater useful surface at end 20 for the coupling with the target. In particular, the inner diameter 22 of end 20 of termination 18 is greater, up to a maximum of 20%, preferably about 10%, with respect to the inner diameter 24 of the central portion 6 of the tubular conduit 4.

Alternatively, termination 18 may also have a cylindrical shape such that the inner diameter 22 of end 20 is substantially equal to the inner diameter 24 of the central portion 6 of the tubular conduit 4.

Suitably, the tools used in the endourologic treatment are inserted into the suction conduit 5 so that their respective end projects from termination 18 of the tubular conduit 4 which internally delimits said suction conduit.

Figure 5:
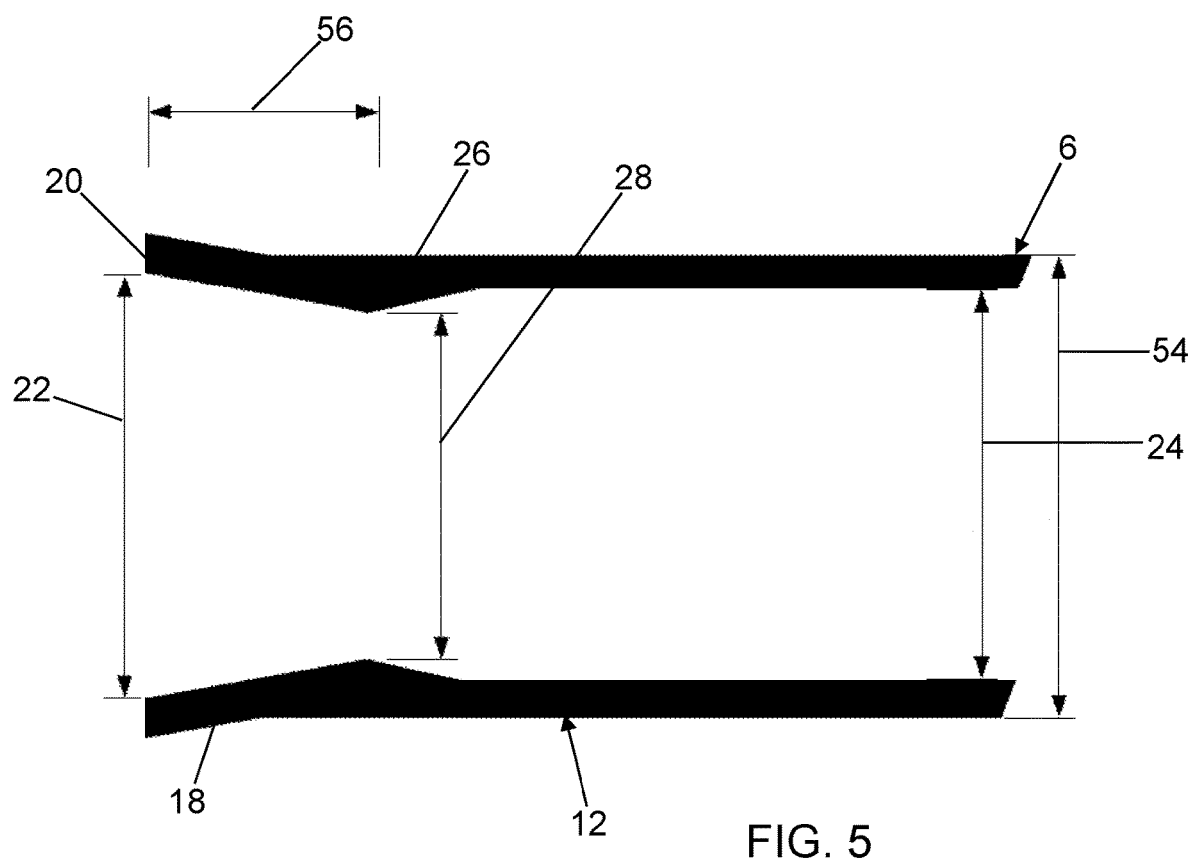
FIG. 5 shows a partial longitudinal section view of an enlarged detail of the device in FIG. 1 without the guide.
Figure 6:
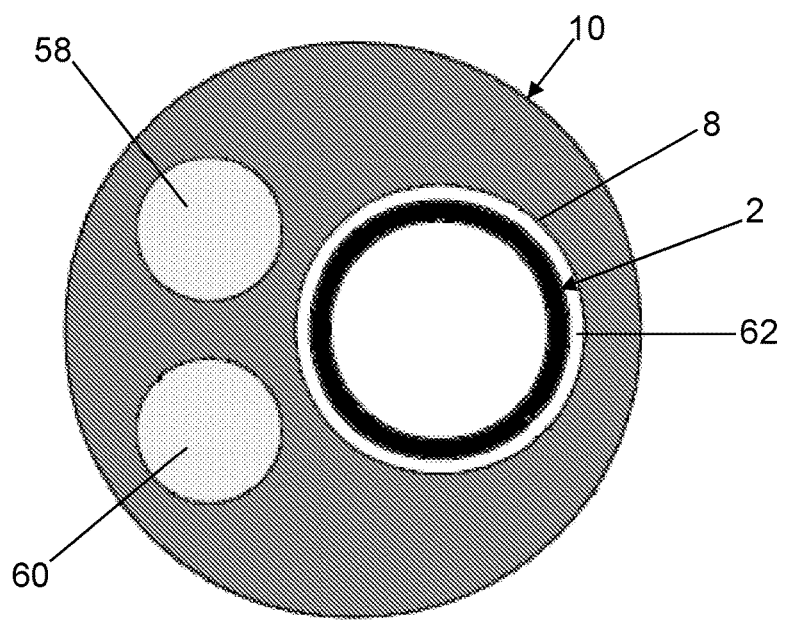
FIG. 6 shows a cross-section view of an endoscope, in which the device in FIG. 1 can be inserted.

Moreover, as shown in FIG. 5, at section 26 from which termination 18 branches off, the inner diameter 28 of the distal portion 12 narrows, preferably by about 10%, with respect to the inner diameter 24 of the central portion 6. This prevents the entry into the tubular conduit 4 of stones, or fragments thereof or other biological or fluid components, having a size comparable to that of the inner diameter of said conduit 4. Suitably, the part of distal portion 12 that is not affected by termination 18 and by the narrowing section 26 has an inner diameter substantially equal to the inner diameter 24 of the central portion 6 of the tubular conduit 4.

The tubular conduit 4 has transverse non-deformability features substantially equal and constant across the longitudinal development thereof; however, suitably, termination 18 of the distal portion 12 may be transversely deformable.

Preferably, at least termination 18 of the distal portion 12 comprises a coil of unifilar Nitinol immersed in soft polyurethane (soft PU) coated with a hydrophilic film.

The proximal portion 14 of conduit 4, that is, the opposite portion with respect to the distal one 12, comprises a first connector 30 for the connection to suction means, such as a vacuum generator. Moreover, the proximal portion 14 comprises a second connector 32 for the connection to the operating channel 8 of endoscope 10; preferably, the latter is movable along the longitudinal development direction of the tubular conduit 4 and in this way, the length of the proximal portion 14 projecting from endoscope 10 can be adjusted.

Both connectors are coaxial to the development direction of the tubular conduit 4. More in detail, moreover, connectors 30 and 32 comprise means (30*a*, 32*a*, respectively), for example consisting of a threaded area, for the attachment to respective couplings, and means (30*b*, 32*b*) for allowing and facilitating the grip of each connector by the surgeon or the operator.

Preferably, the proximal portion 14 is made of thermoplastic material, such as PE.

Moreover, the proximal portion 14 of the tubular conduit 4 comprises a tubular section 34, which bifurcates with respect to the main section 36, to define a lateral access intended for the introduction of a laser fiber 33 within the lumen of the tubular conduit 4 (see FIG. 7). In particular, at the entrance of this bifurcated section 34, a valve 38 is provided for the adjustment and maintenance of a negative pressure within the lumen of the tubular conduit 4 in order to prevent the interruption of the suction made by the device itself.

Around the outer surface of the tubular conduit 4 of device 2, a cylindrical body 40 is applied which acts as a safety lock for inserting the device itself into endoscope 10.

Preferably, device 2 according to the invention also comprises an inner guide 42 removably insertable into the tubular conduit 4 to insert the latter into the operating channel 8 of endoscope 10.

In particular, the inner guide 42 comprises a rod which can be removably inserted within the tubular conduit 4 which is advantageously provided at the distal end thereof with means for keeping the tubular conduit extended during the insertion step of the latter within the operating channel 8 of endoscope 10. Preferably, the rod of guide 42 has a termination with two diametric appendages 44 intended to fit into corresponding diametrically opposed rings 46 provided at the end of termination 18 of the distal portion 12. Preferably, guide 42 is made of substantially rigid PE.

In particular, guide 42 comprises:

a proximal portion 47 with a connector 48 thereof for the attachment to connector 30 of the tubular conduit 4; in particular, also connector 48 comprises means 48a (such as a threaded section) for the attachment of connector 30, and means for gripping by the surgeon or operator;

a central portion 50 intended to cross the central portion 6 and part of the distal portion 12 of the tubular conduit 4; in particular, portion 50 develops substantially by the entire length of the central portion 6 of the tubular conduit 4 and has a section just smaller than the inner diameter 24 of the central portion itself, a distal portion 52 intended to cross termination 18 of the distal portion 12 of the tubular conduit 4; in particular, portion 52 has a slightly smaller section than the inner section 24 of the tubular conduit 4 in order to overcome the shrinkage defined at section 26.

The dimensions of device 2 depend on the type of endoscope used and in any event, the outer diameter 54 of the central portion 6 of the tubular conduit 4 ranges between about 1 mm (equal to 3Fr) and about 10 mm.

Moreover, the length of the central portion 6 of the tubular conduit 4 is substantially at least 1 mm longer than the length of the operating channel 8 of endoscope 10; in particular, in the case of flexible uretero-nephroscopes, such a length is equal to about 681 mm.

The proximal portion 14 of the tubular conduit 4 may be any length and, by way of example only, it may be of between 5 and 10 cm.

More in detail, in the case of a device 2 in which the outer diameter 54 of the central portion 6 of the tubular conduit 4 is between 1 mm and 10 mm, preferably about 1 mm (i.e. about 3Fr), the inner diameter 24 of said portion is preferably about 0.8 mm, the inner diameter 28 at the narrowing section 26 is about 0.72 mm while at end 20, diameter 22 is about 0.9 mm; in addition, preferably, with said sizes, length 56 of termination 18 is about 0.5 mm.

Device 2 according to the invention can be used with any endoscopic instrument provided with one or more operating channels, and with further support channels 58 and 60, respectively, for lighting and for the optical fibers. For example, these endoscopic instruments include a flexible uretero-nephroscope for kidney stones, a rigid or flexible cystoscope for bladder stones, a rigid ureteroscope for ureteral stones and a rigid or flexible nephroscope for kidney or ureteral stones.

The operation of device 2 according to the invention clearly appears from the foregoing.

At first, the inner guide 42 is inserted into the tubular conduit 4 and is locked, through connector 48 thereof, to connector 30 of said conduit. Then, device 2 thus configured can be easily inserted through the operating channel 8 of endoscope 10 and can allow the distal portion 6 to project from the end of the endoscope inserted into the patient's body.

The inner guide 42 of device 2 substantially serves to facilitate the introduction of the device itself within endoscope 10. In fact, the inner guide 42 keeps device 2 always extended and thus prevents it from swelling due to the compression thrust necessary for its insertion within the operating channel 8.

Once device 2 has been completely introduced into endoscope 10, the inner guide 42 of device 2 is extracted from the tubular conduit 4. In particular, during the insertion of device 2, guide 42 is fixed by its connector 48 to connector 30 of the tubular conduit 4. Once said insertion step has finished, connector 48 of guide 42 is disconnected from connector 30 of the tubular conduit 4 and the guide itself is extracted from the tubular conduit 4 so that connector 30 of the proximal portion 14 of the tubular conduit 4 can be connected to the coupling of the suction means.

At this point, the surgeon/operator can maneuver endoscope 10 until he reaches the stone and, once reached, he activates the suction means which through the suction flow first attract and then retain the stone at end 20 of termination 18 of the distal portion 6 of device 2. Moreover, if it is necessary to release and remove the fragment from the distal end 6 of device 2, it is sufficient to stop the suction.

Then, always through the suction, the stone thus retained may be mobilized as needed or be extracted from the urinary excretory way. More in detail, once the stone has been captured at end 20 of device 2, the surgeon may remove endoscope 10 from the patient's body and simultaneously extract the stone retained by device 2 inserted into the operating channel 8 of the endoscope itself.

As said, if clinically indicated, it is also possible to introduce, through the bifurcated section 34, within the suction conduit 5, which is delimited by the tubular conduit 4, a laser fiber 33 or other surgical tools (see FIGS. 7 and 8).

Advantageously, the insertion of the laser fiber 33 within the suction conduit 5 allows the laser fragmentation of the stone, while the lithiasic powder thus produced is suctioned by the suction means within the suction conduit 5 defined by the tubular conduit 4. Suitably, the laser fiber 33 may also be used for treatments other than calculosis, for example, it may be used at modulated frequency and energy for the ablation of the excretory pathway lesions.

More in detail, as shown in FIG. 7, the laser fiber 33 is inserted into the suction conduit 5 through the bifurcated section 34 and at the outer end of the latter, a suitable coupling element 35 with the outer fiber 37 associated with a laser generator (not shown) is provided. Suitably, the laser fiber 33 is inserted into the suction conduit 5 so that end 39 thereof projects from termination 18 of the tubular conduit 4.

Advantageously, into the suction conduit 5 delimited by the tubular conduit 4, gripping tools may be introduced, such as baskets, for capturing and retaining the stone or any foreign bodies, so as to facilitate its extraction from the urinary excretory pathway. Moreover, when required, within the suction conduit 5 delimited by the tubular conduit 4, dedicated grippers may be introduced to perform biopsies. Suitably, the gripping tool is inserted into the suction conduit 5 so as to project from termination 18 of the tubular conduit 4.

Advantageously, within the suction conduit 5 delimited by the tubular conduit 4, a catheter 41 for injecting substances may be introduced in order to perform a topical treatment, such as chemotherapy, haemostatic, contrast graphic, drainage or other. Suitably, catheter 41 is inserted into the suction conduit 5 so that end 43 thereof projects from termination 18 of the tubular conduit 4. More in detail, as shown in FIG. 8, catheter 41 is inserted into the suction conduit 5 through the bifurcated section 34 and at the outer end of the latter, a suitable coupling element 45 is provided.

In addition, outside the bifurcated section 34, catheter 41 has a first fitting 47 for a syringe 51 or for suitable single or multi-port injection systems, and a second fitting 49 to which a closing cap 53 is suitably applied.

Suitably, in the case, not shown herein, in which endoscope 10 has a double operating channel, the irrigation of the treated site takes place through a second dedicated channel, which is different from channel 8 in which device 2 is inserted. Instead, in the case of endoscope 10 provided with a single operating channel 8, the irrigation takes place through the annular space 62 defined between the outer wall of the tubular conduit 4 and the inner wall of the operating channel 8. In this regard, the tubular conduit 4 suitably has an outer diameter 54 which is about 10% smaller than the inner diameter of the operating channel 8.

Advantageously, the truncated cone shape of termination 8 of the distal portion 12 and the narrowing defined at section 26 of the distal portion itself allow on the one hand facilitating the coupling with the stone by increasing the contact surface therewith, and on the other hand allow the entry within the central portion 6 only of the fragments that have a smaller size than the diameter of the inner lumen of the central portion itself, and this prevents larger fragments from getting jammed along conduit 4.

In any case, should a fragment get jammed, the suction means may be disconnected from connector 30 of the proximal portion 14 in order to insert a guide or other means suitable for removing the fragment.

From the foregoing it is apparent that the mini-invasive device, according to the invention for the endourologic treatment, is particularly advantageous since:

it has features that will not hamper the flexibility of the endoscopic tool, it is able to reach the most peripheral districts of the urinary tract;

it uses suction as a tractive force, and in this way it allows to attract stone fragments of various sizes, even small and distant ones that are difficult to be removed with conventional devices;

it allows an easy and immediate suction, even for distant stones, thus preventing the laborious maneuvering required by traditional devices for removing the stone fragment;

it is able to attract at its distal end the stone fragments to be mobilized or removed;

it may allow the suction of the lithiasic powder obtained during a contextual lithotripsy performed by introducing a laser fiber inside the device itself;

it can be used with a plurality of instruments used in the endourologic treatment, and in particular with a laser source for lithotripsy, a gripping tool and/or with a catheter for injecting substances, it allows stopping the retention of the stone fragment at any time simply by stopping the suction;

it drastically reduces the need to replace, during the same endourologic intervention, the device in use with another device, by virtue of its simple construction, it allows saving on production costs.

In particular, the mini-invasive device according to the invention is more advantageous than conventional ones because:

unlike what is described in US 2004/0019358, it provides for the possibility of inserting a surgical instrument within the suction conduit itself, unlike what described in U.S. Pat. No. 4,692,139 (which still has an outer sleeve that is in no way comparable to an endoscope), it provides that the distal portion of the suction conduit projects from the distal tip of the endoscope in order to come close to the target to be mobilized or removed; moreover, unlike U.S. Pat. No. 7,540,868, the device according to the invention provides for the possibility of inserting, within the same suction conduit, not only the laser and the catheter for injecting substances, but also gripping tools, such as grippers or baskets;

unlike those described in U.S. Pat. No. 5,102,415, WO 99/45835, US 2002/188313, WO 2012/156924 and DE 19842113, which however are not used in the endourologic context, is adapted to be inserted within an endoscope, unlike what described in U.S. Pat. No. 6,375,651, the laser (which is an instrument used in the endourologic treatment) can be removably inserted within the suction conduit; moreover, unlike U.S. Pat. No. 6,375,651, in which the suction conduit is delimited by a partition element, in the device according to the invention the suction conduit is advantageously entirely and only delimited by the inner walls of the tubular casing, and this greatly simplifies the manufacture of the device itself, unlike what described in U.S. Pat. No. 5,417,697, it provides for the possibility of inserting, within the suction conduit, not a cauterization ring but a laser source for lithotripsy, a gripping tool and/or a catheter 41 for injecting substances, while unlike U.S. Pat. No. 7,540,868, it provides for the possibility of inserting, within the same suction conduit, not only the laser, but also gripping tools, such as grippers or baskets; also, unlike U.S. Pat. Nos. 7,540,868, 7,540,868 and DE 19842113, in the device according to the invention the tubular conduit is substantially non-deformable, and advantageously, it has a proximal portion that includes a connector for direct connection to the suction means, without requiring any intermediate suction tube, and this greatly simplifies the manufacture of the device itself, unlike the solutions described in all the documents mentioned above, its distal portion has a transverse narrowing in order to prevent the entry of components or fragments within the tubular conduit which may get jammed within the conduit itself, unlike the solutions described in all the documents mentioned above, it also comprises an inner guide removably insertable within the tubular conduit in order to insert the latter within the operating channel of the endoscope.

The mini-invasive device according to the invention has been described and is particularly suitable for the treatment of urolithiasis; it however can be used for other urological endoscopic treatments, such as the removal of bladder, intrarenal or ureteral stones, carried out by the various types of endoscopes that are currently available or, more broadly, it can be used for the suction of the results of laser treatments, also on tissues, carried out through the laser fiber that can be introduced within the suction conduit provided in the device.

In another aspect, the invention relates to an endoscope (10) for endourologic treatment that has at least one operating channel (8), within which a mini-invasive device (2) according to one of the previously described embodiments is inserted.

In one embodiment, the operating channel (8) of the endoscope has a greater diameter than the tubular conduit (4).

An endoscope (10) according to the invention may include at least an additional operating support channel (58, 60) for a lighting device and/or an optical means of image acquisition and transmission.

An endoscope according to the invention may also include an additional operating channel, separated from the operating channel (8) in which the tubular conduit (4) is inserted, for irrigating the treated site.

The irrigation of the treated site may take place through an annular space (62) defined between the outer wall of the tubular conduit (4) and the inner wall of the operating channel (8).

The invention claimed is:

1. A mini-invasive device (2) for endourologic treatment, comprising:
a tubular conduit (4), configured to be inserted through and along an operating channel (8) of an endoscope (10),
wherein said tubular conduit (4):
defines an inner lumen,
has a proximal portion (14) comprising a first connector (30) adapted to connect to a suction device,
has a distal portion (12) adapted to project from a distal tip of said endoscope (10), and
internally delimits a suction conduit (5) adapted to receive at least one tool (33, 41) to be used in the endourologic treatment,
wherein said mini-invasive device further comprises an inner guide (42) adapted to be removably inserted within said tubular conduit (4) to carry out an insertion of said tubular conduit (4) within the operating channel (8) of the endoscope (10), said inner guide (42) comprising a rod extending from the proximal portion to the distal portion of the tubular conduit when the rod is inserted into the tubular conduit, means being provided for removably engaging a distal end of the rod with the distal portion of the tubular conduit so as to keep the tubular conduit (4) extended during the insertion thereof within the operating channel (8) of the endoscope (10), and
wherein the proximal portion (14) of said tubular conduit (4) comprises a second connector (32), longitudinally movable along the tubular conduit (4), adapted to connect the endoscope (10) to the operating channel (8), and locking the mini-invasive device (2) within said endoscope (10).

2. The mini-invasive device according to claim 1, wherein the suction conduit is adapted to receive at least one of the following tools: a laser source (33) for lithotripsy, a gripping tool, or a catheter (41) for injecting substances.

3. The mini-invasive device according to claim 1, wherein said suction conduit (5), adapted to receive said at least one tool (33, 41) used in the endourologic treatment, is entirely and solely delimited by an inner wall of said tubular conduit (4).

4. The mini-invasive device according to claim 1, wherein said at least one tool (33, 41) used in the endourologic treatment is inserted within the suction conduit (5) so that a distal end of said at least one tool projects from a distal end (18) of the tubular conduit (4,) which internally delimits said suction conduit (5).

5. The mini-invasive device according to claim 1, wherein the distal portion (12) of the tubular conduit (4) has greater longitudinal flexibility than a longitudinal flexibility of one or both of a central portion (6) or of said proximal portion (14) of said tubular conduit (4).

6. The mini-invasive device according to claim 1, wherein said tubular conduit (4) comprises a distal tip (18) that internally defines a deformable lumen.

7. The mini-invasive device according to claim 1, wherein said distal portion (12) has a cylindrical distal tip having a diameter (22), at an end (20) thereof, equal to an inner diameter (24) of a central portion (6) of the tubular conduit (4).

8. The mini-invasive device according to claim 1, wherein said distal portion (12) has a frusto-conical distal tip (18) with a diameter that is greater no more than 20% than an inner diameter (24) of a central portion (6) of the tubular conduit (4).

9. The mini-invasive device according to claim 1, wherein the distal portion (12) of said tubular conduit (4) comprises a section (26), of which an inner diameter (28) becomes narrower with respect to an inner diameter (24) of a central portion (6) of said tubular conduit.

10. The mini-invasive device according to claim 1, wherein the tubular conduit (4) is internally associated with a reinforcement armor (16), and wherein said reinforcement armor (16) extends along a majority or an entirety of the tubular conduit (4).

11. The mini-invasive device according to claim 1, wherein the proximal portion (14) of said tubular conduit (4) comprises a tubular section (34) that bifurcates with respect to a main section of said tubular conduit (4) and thus defines a lateral access for introduction, within the suction conduit (5) delimited by said tubular conduit (4), of said at least one tool used in the endourologic treatment.

12. The mini-invasive device according to claim 11, wherein said bifurcated tubular section (34) comprises a valve (38) adapted to adjust and maintain pressure within a lumen of the suction conduit (5) defined by said tubular conduit (4).

13. The mini-invasive device according to claim 1, wherein said first connector (30) comprises first connector attachment members (30a) for attaching the suction device, and second connector members (30b) adapted to enable and facilitate gripping of said first connector by a surgeon or an operator.

14. The mini-invasive device according to claim 1, wherein said second connector (32) comprises first connector attachment members (32a) for attaching the operating channel (8) of the endoscope (10), and second connector attachment members (32b) adapted to enable and facilitate gripping of said second connector by a surgeon or an operator.

15. The mini-invasive device according to claim 1, wherein said rod is configured to be reversibly inserted within said tubular conduit (4) and is provided with members for attachment of said rod to an end of the distal portion (12) of said tubular conduit (4).

16. The mini-invasive device according to claim 1, wherein said inner guide (42) is provided with a third connector (48) for connection to the tubular conduit (4).

17. An endoscope (10) for endourologic treatment, comprising:
at least one operating channel (8), within which a mini-invasive device (2) is inserted, the mini-invasive device comprising:
a tubular conduit (4), configured to be inserted through and along an operating channel (8) of the endoscope (10),
wherein the tubular conduit (4):
defines an inner lumen,
has a proximal portion (14) comprising a first connector (30) adapted to connect to a suction device,
has a distal portion (12) adapted to project from a distal tip of the endoscope (10), internally delimits a suction conduit (5) adapted to receive at least one tool (33, 41) to be used in the endourologic treatment; and an inner guide (42) adapted to be removably inserted within the tubular conduit (4) to carry out an insertion of the tubular conduit (4) within the operating channel (8) of the endoscope (10), the inner guide (42) comprising a rod extending from the proximal portion to the distal portion of the tubular conduit when the rod is inserted into the tubular conduit, means being provided for removably engaging a distal end of the rod with the distal portion of the tubular conduit so as to keep the tubular conduit (4) extended during the insertion thereof within the operating channel (8) of the endoscope (10), wherein the proximal portion (14) of said tubular conduit (4) comprises a second connector (32), longitudinally movable along the tubular conduit (4), adapted to connect the endoscope (10) to the operating channel (8), and locking the mini-invasive device (2) within said endoscope (10).

18. The endoscope (10) according to claim 17, further comprising at least a second operating support channel (58, 60) for one or both of a lighting device or an optical device of image acquisition and transmission.

19. The endoscope according to claim 17, further comprising a second operating channel, separated from the operating channel (8) in which said tubular conduit (4) is inserted, for irrigating a treated site.

* * * * *